(12) United States Patent
Muramatsu et al.

(10) Patent No.: US 10,895,535 B2
(45) Date of Patent: Jan. 19, 2021

(54) MEASUREMENT METHOD, AND MEASURING CHIP AND MEASURING KIT USED FOR THE SAME

(71) Applicant: KONICA MINOLTA, INC., Tokyo (JP)

(72) Inventors: Shinichi Muramatsu, Hino (JP); Keizou Takano, Osaka (JP)

(73) Assignee: KONICA MINOLTA, INC., Tokyo (JP)

( * ) Notice: Subject to any disclaimer, the term of this patent is extended or adjusted under 35 U.S.C. 154(b) by 247 days.

(21) Appl. No.: 15/739,435

(22) PCT Filed: Jun. 10, 2016

(86) PCT No.: PCT/JP2016/067364
§ 371 (c)(1),
(2) Date: Dec. 22, 2017

(87) PCT Pub. No.: WO2016/208421
PCT Pub. Date: Dec. 29, 2016

(65) Prior Publication Data
US 2018/0180545 A1 Jun. 28, 2018

(30) Foreign Application Priority Data

Jun. 24, 2015 (JP) ................................. 2015-126748

(51) Int. Cl.
*G01N 21/64* (2006.01)
*G01N 33/553* (2006.01)
(Continued)

(52) U.S. Cl.
CPC ....... *G01N 21/6428* (2013.01); *G01N 21/554* (2013.01); *G01N 21/64* (2013.01);
(Continued)

(58) Field of Classification Search
None
See application file for complete search history.

(56) References Cited

U.S. PATENT DOCUMENTS

2010/0009458 A1* 1/2010 Ohtsuka ............ G01N 21/6428
436/166
2014/0186216 A1 7/2014 Campbell et al.

FOREIGN PATENT DOCUMENTS

| JP | H06324043 A | 11/1994 |
|---|---|---|
| JP | 08-141044 A | 11/1997 |

(Continued)

OTHER PUBLICATIONS

Extended European Search Report corresponding to Application No. 16814192.7-1118 PCT/JP2016067364; dated Feb. 27, 2018.
(Continued)

*Primary Examiner* — Rebecca M Giere
(74) *Attorney, Agent, or Firm* — Cantor Colburn LLP (57) ABSTRACT

Provided is a measurement method with which an analyte in a sample containing a high concentration of the analyte can be measured with high accuracy without diluting the sample in multiple stages. An embodiment of the present invention relates to a measurement method for measuring an amount of an analyte in a sample, the method including: a binding step of providing the sample to a containing part of a measuring chip including the containing part for containing liquid, and a first capture body immobilized inside the containing part and having a recognition site that specifically binds to the analyte so as to bind the analyte contained in the sample to the first capture body; and a measurement step of measuring an amount of the analyte bound to the first capture body. The measurement method includes an adjustment step in which a second capture body having a recognition site that specifically binds to the analyte is bound to a part of the analyte in the sample in parallel with the binding
(Continued)

step or before the binding step so as to reduce the amount of the analyte capable of binding to the first capture body.

11 Claims, 7 Drawing Sheets

(51) Int. Cl.
*G01N 33/543* (2006.01)
*G01N 21/552* (2014.01)

(52) U.S. Cl.
CPC ......... *G01N 21/645* (2013.01); *G01N 33/543* (2013.01); *G01N 33/553* (2013.01); *G01N 2021/6439* (2013.01); *G01N 2021/6463* (2013.01); *G01N 2201/0635* (2013.01); *G01N 2333/8139* (2013.01)

(56) References Cited

FOREIGN PATENT DOCUMENTS

| | | |
|---|---|---|
| JP | H10185921 A | 7/1998 |
| JP | H10239317 A | 11/1998 |
| JP | 2004191332 A | 7/2004 |
| JP | 2006017745 A | 1/2006 |
| JP | 2009294116 A | 12/2009 |
| JP | 2010019767 A | 1/2010 |
| JP | 2011220768 A | 11/2011 |
| JP | 2012220246 A | 11/2012 |
| JP | 2015021818 A | 2/2015 |
| WO | 2015064704 A1 | 5/2015 |

OTHER PUBLICATIONS

International Search Report corresponding to Application No. PCT/JP2016/067364; dated Aug. 16, 2016.
Written Opinion of the International Searching Authority corresponding to Application No. PCT/JP2016/067364; dated Aug. 16, 2016.
JPO Notice of Reasons for Refusal corresponding to Application No. 2017-525203; dated Nov. 5, 2019.
JPO Notice of Reasons for Refusal corresponding to JP Application No. 2017-525203; dated Apr. 28, 2020.
JPO Notice of Reasons for Refusal for corresponding JP Application No. 2017-525203; dated Aug. 18, 2020.
JPO Notice of Reasons for Refusal for corresponding JP Application No. 2017-525203, dated Nov. 10, 2020.

* cited by examiner

MEASUREMENT METHOD, AND MEASURING CHIP AND MEASURING KIT USED FOR THE SAME

CROSS REFERENCE TO RELATED APPLICATIONS

This is the U.S. national stage of application No. PCT/JP2016/067364, filed on Jun. 10, 2016. Priority under 35 U.S.C. § 119(a) and 35 U.S.C. § 365(b) is claimed from Japanese Applications No. 2015-126748, filed Jun. 24, 2015, the disclosure of which is incorporated herein by reference.

TECHNICAL FIELD

The present invention relates to a method for measuring an amount of an analyte in a sample, and a measuring chip and a measuring kit used for the method.

BACKGROUND ART

In a clinical test and the like, highly sensitive measurement in regard to a trace of an analyte such as protein and DNA makes it possible to quickly understand conditions of a patient so as to treat the patient. Therefore, it is required to provide a highly sensitive and specific method for measuring a trace of an analyte.

Examples of the specific method for measuring an analyte include enzyme-linked immuno sorbent assay ("ELISA"), surface plasmon-field enhanced fluorescence spectroscopy (hereinafter also referred to as the "SPFS"), reflectometric interference spectroscopy (hereinafter also referred to as the "RIfS"), surface plasmon resonance (also referred to as the "SPR"), and quartz crystal microbalance (hereinafter also referred to as the "QCM").

For example, in the SPFS, a capture body (for example, a primary antibody) that can specifically bind to an analyte is immobilized on a metal film, thereby forming a reaction field to capture the analyte. When this reaction field is provided with a sample (for example, blood) containing the analyte, the analyte is immobilized on the reaction field. Next, when the reaction field is provided with a capture body (for example, a secondary antibody) labeled with a fluorescent substance, the analyte immobilized on the reaction field is labeled with the fluorescent substance. When the metal film is irradiated with excitation light in this state, the fluorescent substance that labels the analyte is excited by an electric field enhanced by SPR and emits fluorescence. As the emitted fluorescence is detected, it is possible to detect the presence or amount of the analyte.

In a case where the amount of the analyte in a sample is measured by various measurement methods, not limited to the SPFS, a mass of the analyte contained per unit volume of the sample is usually indicated by a signal amount and the like corresponding to the mass. However, when a concentration of the analyte in the sample is high and exceeds a dynamic range of a measurement apparatus, it is difficult to accurately specify the amount of the analyte. Therefore, in typical measurement, dilution has been performed in multiple stages so that the concentration of the analyte in the sample falls within the dynamic range of the measurement apparatus. Dilution is performed manually or automatically. Furthermore, various metering devices, and multistage dilution devices configured to dilute a sample have been proposed in the related art (for example, Patent Literature 1 and Patent Literature 2).

CITATION LIST

Patent Literature

Patent Literature 1: JP 2012-220246 A
Patent Literature 2: JP 9-304248 A

SUMMARY OF INVENTION

Technical Problem

However, manually performing multistage dilution increases the number of steps, which leads to a complicated operation. Furthermore, manually performing such dilution may cause a human error. Still further, performing multistage dilution of a sample with various metering devices and dilution devices causes not only complication in structure of an apparatus or an increase in size of an apparatus but also an increase in cost.

The present invention has been made in light of such problems, and an object of the present invention is to provide a measurement method, a measuring chip, and a measuring kit capable of measuring an analyte with high accuracy without multistage dilution in regard to a sample containing a high concentration of the analyte.

Solution to Problem

In order to solve at least one of the aforementioned problems, a measurement method according to an embodiment of the present invention, as a method to measure an amount of analyte in a sample, includes: a binding step of binding the analyte contained in the sample to a first capture body immobilized inside a containing part for containing liquid and having a recognition site that specifically binds to the analyte by providing the sample to the containing part of a measuring chip including the containing part and the first capture body; and a measurement step of measuring an amount of the analyte bound to the first capture body, the measurement method further including: an adjustment step of reducing the amount of the analyte capable of binding to the first capture body by binding a second capture body having a recognition site that specifically binds to the analyte to a part of the analyte in the sample in parallel with the binding step or before the binding step.

A measuring chip according to an embodiment of the present invention is for measuring an amount of an analyte in a sample, the measuring chip including: a containing part for containing liquid; a first capture body immobilized on a detection area for detecting an analyte inside the containing part and having a recognition site that specifically binds to the analyte; and a second capture body immobilized on an area out of the detection area inside the containing part and having a recognition site that specifically binds to the analyte.

A measuring kit according to an embodiment of the present invention includes: a measuring chip which includes a containing part for containing liquid, and a first capture body which is immobilized on a detection area for detecting an analyte inside the containing part and has a recognition site that specifically binds to the analyte; and a reagent including a second capture body having a recognition site that specifically binds to a site where the first capture body is to bind in the analyte.

Advantageous Effects of Invention

According to the present invention, in regard to a sample containing a high concentration of an analyte, it is possible to measure an amount of the analyte with high accuracy without diluting the sample in multiple stages. Therefore, it is possible to achieve low-cost, specific, and highly-accurate measurement of the amount of the analyte in the sample.

DESCRIPTION OF EMBODIMENTS

Hereinafter, an embodiment of the present invention will be described in detail with reference to the drawings. As a typical example of a measurement method according to the present invention, described herein is a method for measuring an amount of an analyte contained in a sample with a surface plasmon-field enhanced fluorescence spectrometer (an SPFS apparatus). Note that, however, an embodiment of the present invention is not limited to the method for measuring with the measurement apparatus.

First Embodiment (Chip and Apparatus for Measurement)

Figure 1:
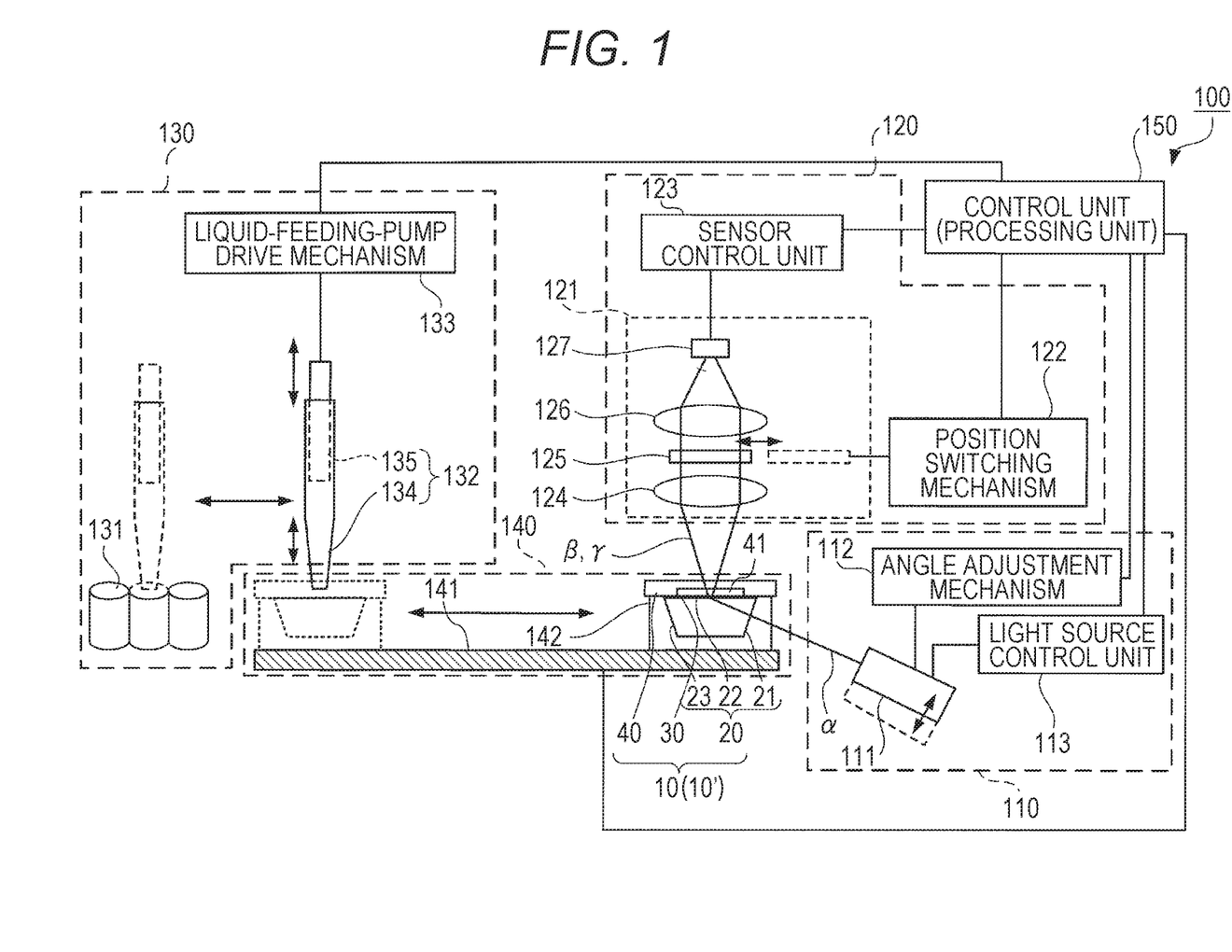
FIG. 1 is a schematic view illustrating a structure of an SPFS apparatus.

FIG. 1 is a schematic view illustrating a structure of an SPFS apparatus 100 used in a first embodiment. As illustrated in FIG. 1, the SPFS apparatus 100 includes an excitation light irradiation unit 110, a fluorescence detection unit 120, a liquid feeding unit 130, a conveyance unit 140, and a control unit 150. In the SPFS apparatus 100, an amount of an analyte in a sample is measured, while a measuring chip 10 is being attached to a chip holder 142 of the conveyance unit 140. The measuring chip 10 used in the first embodiment will now be described, and each component of the SPFS apparatus 100 will be described later.

The measuring chip 10 includes a prism 20 having an incidence surface 21, a film formation surface 22, and a light-emission surface 23; a metal film 30 formed on the film formation surface 22; and a channel cover 40 disposed on the film formation surface 22 or the metal film 30. In the present embodiment, the channel cover 40 has a channel groove on a surface facing the metal film 30, and a space surrounded by the metal film 30 and the channel cover 40 is a containing part 41 configured to contain liquid (for example, a sample). The measuring chip 10 is usually exchanged per analysis. The measuring chip 10 is preferably a structural object having a length of several millimeters to several centimeters on each side, but it may be a smaller structural object or a larger structural object not included in the category of "chip".

The prism 20 includes a dielectric material transparent to excitation light α. The prism 20 has the incidence surface 21, the film formation surface 22, and the light-emission surface 23. The incidence surface 21 allows the excitation light α from the excitation light irradiation unit 110 to enter the prism 20. The metal film 30 is disposed on the film formation surface 22. The excitation light α that has entered the prism 20 is reflected by a back side of the metal film 30, more specifically, an interface (the film formation surface 22) between the prism 20 and the metal film 30, and becomes reflected light. The light-emission surface 23 is a surface for emitting the reflected light out of the prism 20.

The prism 20 is not particularly limited in shape. In the present embodiment, the prism 20 is a pillar-shaped body having a trapezoidal bottom face. A surface corresponding to one base of the trapezoid is the film formation surface 22, a surface corresponding to one leg is the incidence surface 21, and a surface corresponding to the other leg is the light-emission surface 23. A preferable shape of the trapezoidal bottom face is an isosceles trapezoid. Accordingly, the incidence surface 21 and the light-emission surface 23 become symmetric to each other, which makes it difficult to retain an S-wave component of the excitation light α inside the prism 20.

The incidence surface 21 is formed so that the excitation light α does not return to the excitation light irradiation unit 110. In a case where a light source of the excitation light α is a laser diode (hereinafter also referred to as "LD"), a return of the excitation light α to the LD disturbs the excited state of the LD, which leads to fluctuations in a wavelength and output of the excitation light α. Therefore, in a changing range centering on an ideal resonance angle or enhancement angle, an angle of the incidence surface 21 is set so that the excitation light α does not enter the incidence surface 21 perpendicularly. Herein, the "resonance angle" indicates an angle of incidence when light intensity of the reflected light emitted from the light-emission surface 23 is minimized in changing an angle of incidence of the excitation light α with respect to the metal film 30. Furthermore, the "enhancement angle" indicates an angle of incidence when light intensity of scattering light γ (hereinafter referred to as "plasmon scattering light") having a wavelength similar to that of the excitation light α emitted above the measuring chip 10 is maximized in changing the angle of incidence of the excitation light α with respect to the metal film 30. In the present embodiment, an angle between the incidence surface 21 and the film formation surface 22 and an angle between the film formation surface 22 and the light-emission surface 23 are both about 80 degrees.

The resonance angle (and the enhancement angle in the immediate vicinity thereof) is roughly determined by the design of the measuring chip 10. Elements relative to the design are, for example, a refractive index of the prism 20, a refractive index of the metal film 30, a film thickness of the metal film 30, an extinction coefficient of the metal film 30, and a wavelength of the excitation light α. The resonance angle and the enhancement angle are shifted by the analyte captured on the metal film 30 through a first capture body, but a shift amount is less than several degrees.

The prism 20 has birefringence properties to no small extent. Examples of a material of the prism 20 include resin and glass. The material of the prism 20 is preferably a resin having a refractive index of 1.4 to 1.6 and small birefringence.

The metal film 30 is disposed on the film formation surface 22 of the prism 20. Accordingly, an interaction (SPR) occurs between free electrons in the metal film 30 and photons in the excitation light α incident upon the film formation surface 22 under the total reflection conditions, which makes it possible to generate localized field light (commonly referred to as "evanescent light" or "near-field light") on a surface of the metal film 30.

A material of the metal film 30 is not particularly limited as long as it is a metal capable of causing surface plasmon resonance. Examples of the material of the metal film 30 include gold, silver, copper, aluminum, and alloys of these materials. A method for forming the metal film 30 is not particularly limited. Examples of the method for forming the metal film 30 include sputtering, vapor deposition, and plating. A thickness of the metal film 30 is not particularly limited, but it is preferably within the range of 30 to 70 nm.

Although not illustrated in FIG. 1, the first capture body for capturing the analyte is immobilized on a detection area in a surface of the metal film 30 not facing the prism 20 (the surface of the metal film 30). The "detection area" is provided to detect the analyte by the SPFS apparatus 100. The back side of the metal film 30 corresponding to the detection area is irradiated with the excitation light α from a light source unit 111. The first capture body immobilized on the detection area has a recognition site that specifically binds to the analyte in the sample. Therefore, when the sample is provided to the containing part 41, the analyte selectively binds to the first capture body. In other words, the analyte can be immobilized on the metal film 30. The first capture body is not limited to a particular type as long as it has a recognition site that specifically binds to the analyte. The first capture body may be a biomolecule that specifically binds to the analyte (for example, a monoclonal antibody, polyclonal antibody, and nucleic-acid aptamer), or may be a fragment of the biomolecule. A method for immobilizing the first capture body on the metal film 30 is not particularly limited, and may be any of physical adsorption, chemical binding (amide coupling, reaction between Au and thiol, or silane coupling), and the like.

The channel cover 40 of the measuring chip 10 is disposed on the metal film 30. Furthermore, the channel cover 40 has the channel groove, and the space (the containing part 41) configured to contain liquid is formed by a wall surface and a top face of the channel groove and by the metal film 30. In a case where the metal film 30 is formed only on a part of the film formation surface 22 of the prism 20, the channel cover 40 may also be disposed on the film formation surface 22. In such a case, the containing part 41 may be a space formed by the wall surface and the top face of the channel groove of the channel cover 40, by the metal film 30, and by the film formation surface 22 of the prism 20. The containing part 41 is not limited in shape and size. The containing part 41 may be a space configured to store liquid temporarily, such as a well. However, from a viewpoint of measurement efficiency, the containing part 41 in the present embodiment is preferably a channel configured to flow liquid. When the containing part 41 is configured as a channel, both ends or one end of the containing part 41 is connected to an inlet and an outlet formed on the top face of the channel cover 40 (both of them are not illustrated).

The channel cover 40 preferably includes a material transparent to the fluorescence β and the plasmon scattering light γ emitted from the metal film 30. An example of the material of the channel cover 40 includes resin. As long as a portion from which the fluorescence β and the plasmon scattering light γ are extracted to the outside is transparent to the fluorescence β and the plasmon scattering light γ, other portions of the channel cover 40 may include an opaque material. The channel cover 40 is bonded to the metal film 30 or the prism 20 by, for example, adhesion with a double-sided tape or an adhesive, laser welding, ultrasonic welding, and pressure bonding using a clamp member.

In the present embodiment, liquid to be provided to the containing part 41 (hereinafter also referred to as the "channel 41") is, for example, a mixed solution of the sample and a second capture body, a labeling solution containing a capture body labeled with a fluorescent substance, and a cleaning solution, as will be described later. Since the first capture body immobilized on the metal film 30 is exposed inside the containing part 41, when the liquid is injected into the channel 41, the liquid comes into contact with the first capture body, causing various reactions and cleaning (removal of impurities).

In the measurement method described later, the analyte is immobilized on the detection area of the measuring chip 10 through the first capture body. Furthermore, the analyte is labeled with a fluorescent substance and the like. Then, as illustrated in FIG. 1, the metal film 30 of the measuring chip 10 is irradiated with the excitation light α at an angle at which SPR occurs to generate localized field light on the metal film 30. With this localized field light, the fluorescent substance is excited and the fluorescent substance emits the fluorescence β. Measurement of light intensity of this fluorescence β specifies the amount of the analyte immobilized on the metal film 30.

Hereinafter, components other than the measuring chip of the SPFS apparatus 100 will be described. As described above, the SPFS apparatus 100 includes the excitation light irradiation unit 110, the fluorescence detection unit 120, the liquid feeding unit 130, the conveyance unit 140, and the control unit 150.

The excitation light irradiation unit 110 irradiates the measuring chip 10 held by the chip holder 142 with the excitation light α. In measuring the fluorescence β or the plasmon scattering light γ, the excitation light irradiation unit 110 emits only P waves with respect to the metal film 30 toward the incidence surface 21 so that the angle of incidence with respect to the metal film 30 forms an angle causing SPR. Herein, the "excitation light" is light which directly or indirectly excites the fluorescent substance. For example, the excitation light α is light causing localized field light that excites the fluorescent substance on the surface of the metal film 30 when irradiating at an angle at which SPR occurs on the metal film 30 through the prism 20. The excitation light irradiation unit 110 includes the light source unit 111, an angle adjustment mechanism 112, and a light source control unit 113.

The light source unit 111 emits the excitation light α being collimated and having a constant wavelength and light intensity in such a manner that the shape of an irradiation spot on the back side of the metal film 30 is substantially circular. The light source unit 111 includes, for example, a light source of the excitation light α, a beam forming optical system, an APC mechanism, and a temperature adjustment mechanism (none of them is illustrated).

The light source is not limited to a particular type, and may be, for example, a laser diode (LD). Other examples of the light source include light emitting diodes, mercury lamps, and other laser light sources. In a case where light emitted from the light source is not a beam, the light emitted from the light source is converted into a beam by a lens, a mirror, a slit, and the like. In a case where light emitted from the light source is not monochromatic light, the light emitted from the light source is converted into monochromatic light by a diffraction grating and the like. Furthermore, in a case where light emitted from the light source is not linearly polarized light, the light emitted from the light source is converted into linearly polarized light by a polarizer and the like.

The beam forming optical system includes, for example, a collimator, a band-pass filter, a linear polarizing filter, a half-wave plate, a slit, zooming means, and the like. The beam forming optical system may include all or part of the aforementioned members. The collimator collimates the excitation light $\alpha$ emitted from the light source. The band-pass filter converts the excitation light $\alpha$ emitted from the light source into narrow band light having only a center wavelength. This is because the excitation light $\alpha$ from the light source has a slight wavelength distribution width. The linear polarizing filter converts the excitation light $\alpha$ emitted from the light source into completely linearly polarized light. The half-wave plate adjusts a polarization direction of the excitation light $\alpha$ so that a P-wave component enters the metal film 30. The slit and the zooming means adjust a beam diameter and a profile shape of the excitation light $\alpha$ such that the irradiation spot on the back side of the metal film 30 is a circle having a predetermined size.

The APC mechanism controls the light source to make output of the light source constant. More specifically, the APC mechanism detects light intensity of light branched from the excitation light $\alpha$ with a photodiode (not illustrated) and the like. Then, the APC mechanism controls input energy by a regression circuit, thereby controlling the output of the light source to be constant.

The temperature adjustment mechanism is, for example, a heater or a Peltier element. The wavelength and the energy of the light emitted from the light source may vary depending on temperatures. For this reason, keeping the temperature of the light source constant by the temperature adjustment mechanism stabilizes the wavelength and the energy of the light emitted from the light source.

The angle adjustment mechanism 112 adjusts the angle of incidence of the excitation light $\alpha$ with respect to the metal film 30 (the interface between the prism 20 and the metal film 30 (the film formation surface 22)). In order to irradiate a prescribed position of the metal film 30 with the excitation light $\alpha$ at a predetermined angle of incidence through the prism 20, the angle adjustment mechanism 112 adjusts an optical axis of the excitation light $\alpha$ and the chip holder 142 to rotate relatively to each other.

For example, the angle adjustment mechanism 112 rotates the light source unit 111 around an axis orthogonal to the optical axis of the excitation light $\alpha$ (an axis perpendicular to the plane of paper in FIG. 1). At this time, a position of a rotation axis is set in such a manner that a position of the irradiation spot on the metal film 30 hardly changes even when changing the angle of incidence. As the position of the rotation center is set close to an intersection point of optical axes of two excitation lights a at both ends of the changing range of the angle of incidence (a point between an irradiation position on the film formation surface 22 and the incidence surface 21), it is possible to minimize a shift of the irradiation position.

As described above, in the angle of incidence of the excitation light $\alpha$ with respect to the metal film 30, the angle at which the light intensity of the plasmon scattering light $\gamma$ is maximized is referred to as the enhancement angle. Setting the angle of incidence of the excitation light $\alpha$ at or near the enhancement angle makes it possible to measure the fluorescence $\beta$ of high intensity. Basic incident conditions of the excitation light $\alpha$ are determined by a material and shape of the prism 20 of the measuring chip 10, a film thickness of the metal film 30, a refractive index of the liquid inside the channel 41, and the like. However, an optimum incident condition slightly varies depending on a type and amount of the fluorescent substance inside the channel 41, a shape error of the prism 20, and the like. For this reason, it is preferable to determine an optimal enhancement angle for each measurement.

The light source control unit 113 controls various devices included in the light source unit 111 so as to control emission of the excitation light $\alpha$ from the light source unit 111. The light source control unit 113 includes, for example, a well-known computer or a microcomputer including an arithmetic device, a control device, a storage device, an input device, and an output device.

The fluorescence detection unit 120 detects the fluorescence $\beta$ generated by irradiating the metal film 30 with the excitation light $\alpha$. As appropriate, the fluorescence detection unit 120 also detects the plasmon scattering light $\gamma$ generated by irradiating the metal film 30 with the excitation light $\alpha$. The fluorescence detection unit 120 includes a light receiving unit 121, a position switching mechanism 122, and a sensor control unit 123.

The light receiving unit 121 is disposed in the normal direction of the metal film 30 of the measuring chip 10. The light receiving unit 121 includes a first lens 124, an optical filter 125, a second lens 126, and a light receiving sensor 127.

The first lens 124 is, for example, a condenser lens configured to condense the light emitted from the metal film 30. The second lens 126 is, for example, an imaging lens configured to form an image on a light receiving surface of the light receiving sensor 127 in accordance with the light condensed by the first lens 124. Light paths between both lenses are substantially parallel to each other. The optical filter 125 is disposed between both lenses.

The optical filter 125 leads only a fluorescent component to the light receiving sensor 127 and removes an excitation light component (plasmon scattering light $\gamma$) in order to detect the fluorescence $\beta$ with a high S/N ratio. Examples of the optical filter 125 include an excitation light reflection filter, a short wavelength cut filter, and a band-pass filter. The optical filter 125 is, for example, a filter including a multi-layer film that reflects a predetermined light component, or a color glass filter that absorbs a predetermined light component.

The light receiving sensor 127 detects the fluorescence $\beta$ and the plasmon scattering light $\gamma$. The light receiving sensor 127 has a high sensitivity capable of detecting weak fluorescence $\beta$ from a very small amount of the analyte. The light receiving sensor 127 is, for example, a photomultiplier tube (PMT) or an avalanche photodiode (APD).

The position switching mechanism 122 switches positions of the optical filter 125 from a position on the light path to a position out of the light path in the light receiving unit 121, or vice versa. Specifically, when the light receiving sensor 127 detects the fluorescence $\beta$, the optical filter 125 is disposed on the light path in the light receiving unit 121, and when the light receiving sensor 127 detects the plasmon scattering light $\gamma$, the optical filter 125 is disposed out of the light path in the light receiving unit 121.

The sensor control unit 123 controls to detect output values of the light receiving sensor 127, to manage sensitivity of the light receiving sensor 127 based on the detected output values, and to change the sensitivity of the light receiving sensor 127 to obtain an appropriate output value.

The sensor control unit 123 includes, for example, a well-known computer or a microcomputer including an arithmetic device, a control device, a storage device, an input device, and an output device.

The liquid feeding unit 130 feeds various kinds of liquid into the channel 41 of the measuring chip 10 held by the chip holder 142. In the present embodiment, for example, a mixed solution of the sample and a second capture body, a labeling solution, and a cleaning solution are fed to the channel 41. The liquid feeding unit 130 includes a liquid chip 131, a syringe pump 132, and a liquid-feeding-pump drive mechanism 133.

The liquid chip 131 is a container configured to contain liquid such as the sample, the labeling solution, the cleaning solution, the second capture body, and a reagent containing these solutions. In regard to a typical liquid chip 131, a plurality of containers is disposed in accordance with types of liquid, or a chip with a plurality of containers being integrated is disposed. Each container included in the liquid chip 131 may contain only one type of solution or may contain plural types of solutions.

The syringe pump 132 in the liquid feeding unit 130 includes a syringe 134, and a plunger 135 configured to reciprocate inside the syringe 134. Due to the reciprocating movement of the plunger 135, the liquid is suctioned and discharged in a quantitative manner. The syringe 134 being replaceable eliminates the need for cleaning the syringe 134. Therefore, it is preferable to make the syringe 134 replaceable from a viewpoint of preventing impurity incorporation and the like. In a case where the syringe 134 is not configured to be replaceable, a structure to clean the inner side of the syringe 134 is added so that the syringe 134 can be used without being replaced with another syringe.

The liquid-feeding-pump drive mechanism 133 includes a driving unit for the plunger 135, and a moving unit for the syringe pump 132. The driving unit for the syringe pump 132 is a device configured to reciprocate the plunger 135, including, for example, a stepper motor. The driving unit including the stepper motor is preferable from a viewpoint of managing an amount of residual liquid in the measuring chip 10 since such a driving unit can manage a feeding amount and feeding speed of the syringe pump 132. The moving unit for the syringe pump 132 freely moves the syringe pump 132 in two directions, for example, in an axial direction (for example, a perpendicular direction) of the syringe 134 and in a direction crossing the axial direction (for example, a horizontal direction). The moving unit for the syringe pump 132 includes, for example, a robot arm, and a two-axis stage or a vertically movable turntable.

The liquid feeding unit 130 suctions various kinds of liquid from the liquid chip 131 and feeds the liquid into the channel 41 of the measuring chip 10. At this time, the plunger 135 is moved to reciprocate the liquid inside the channel 41 in the measuring chip 10 and to stir the liquid inside the channel 41. Accordingly, it is possible to uniform a concentration of the liquid provided inside the channel 41 and to promote a reaction (for example, an antigen-antibody reaction) inside the channel 41. From a viewpoint of performing such operations, it is preferable to arrange the measuring chip 10 and the syringe 134 in such a manner that the inlet of the measuring chip 10 is protected by a multi-layer film and that the syringe 134 is configured to seal the inlet when penetrating this multi-layer film.

The liquid inside the channel 41 is again suctioned by the syringe pump 132 and discharged to the liquid chip 131 and the like. Repeating these operations makes it possible to react various kinds of liquid inside the channel 41, to clean the inner side of the channel 41, and to dispose the analyte labeled with the fluorescent substance in the detection area inside the channel 41.

The conveyance unit 140 conveys the measuring chip 10 to a measurement position or a liquid-feeding position and fixes the measuring chip 10. Herein, the "measurement position" is where the fluorescence detection unit 120 detects the fluorescence $\beta$ or the plasmon scattering light $\gamma$ generated by the excitation light irradiation unit 110 irradiating the measuring chip 10 with the excitation light $\alpha$. Furthermore, the "liquid-feeding position" is where the liquid feeding unit 130 feeds liquid into the channel 41 of the measuring chip 10 or where the liquid feeding unit 130 removes the liquid inside the channel 41 of the measuring chip 10. The conveyance unit 140 includes a conveyance stage 141 and the chip holder 142. The chip holder 142 is fixed on the conveyance stage 141, detachably holding the measuring chip 10. The chip holder 142 is shaped so as to be capable of holding the measuring chip 10 and so as not to obstruct light paths of the excitation light $\alpha$, the fluorescence $\beta$, and the plasmon scattering light $\gamma$. For example, the chip holder 142 is provided with an opening that allows the excitation light $\alpha$, the fluorescence $\beta$, and the plasmon scattering light $\gamma$ to pass therethrough. The conveyance stage 141 moves the chip holder 142 in one direction and in the opposite direction. The conveyance stage 141 is also shaped so as not to obstruct the light paths of the excitation light $\alpha$, the fluorescence $\beta$, and the plasmon scattering light $\gamma$. The conveyance stage 141 is driven by, for example, a stepper motor and the like.

The control unit 150 controls the angle adjustment mechanism 112, the light source control unit 113, the position switching mechanism 122, the sensor control unit 123, the liquid-feeding-pump drive mechanism 133, and the conveyance stage 141. The control unit 150 includes, for example, a well-known computer or a microcomputer including an arithmetic device, a control device, a storage device, an input device, and an output device.

(Measurement Method)

Figure 2:
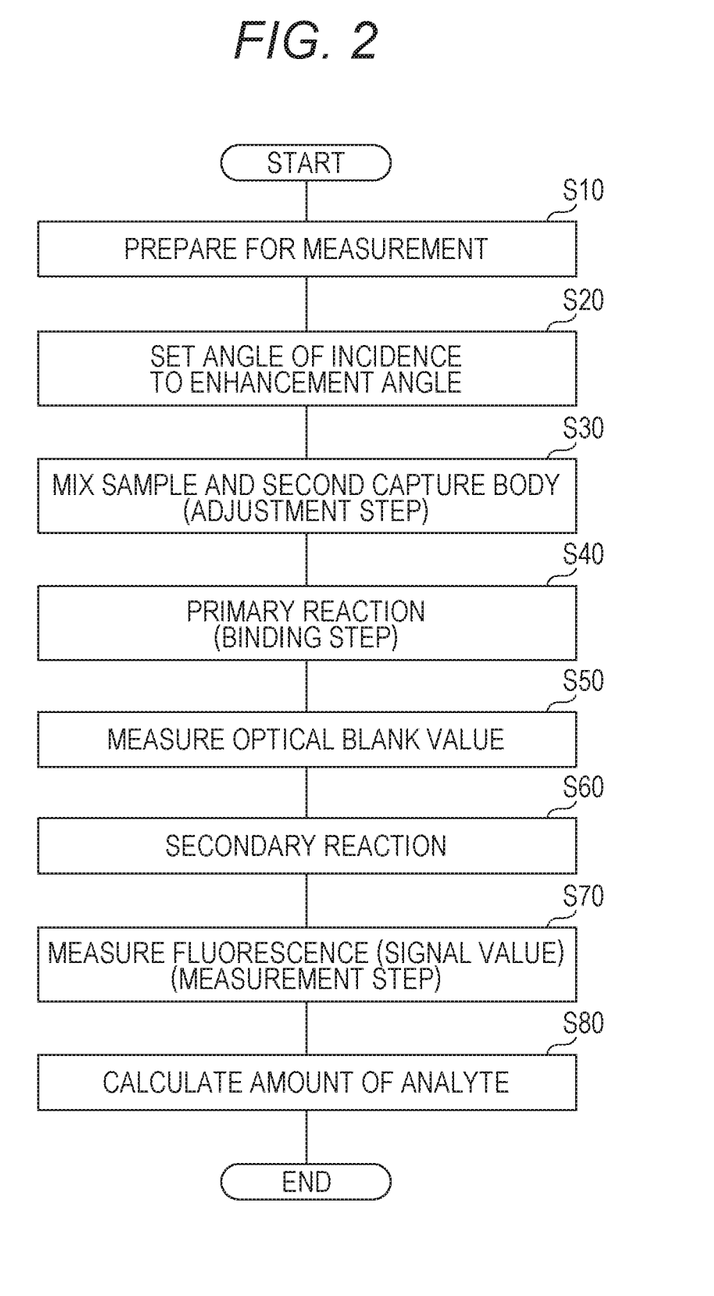
FIG. 2 is a flowchart illustrating an exemplary operation procedure of the SPFS apparatus when performing a measurement method according to a first embodiment of the present invention.

Hereinafter, a measurement method according to the first embodiment will be described. FIG. 2 is a flowchart illustrating an exemplary operation procedure of the SPFS apparatus 100 when performing the measurement method according to the first embodiment.

The first thing is to prepare for measurement (step S10). Specifically, the measuring chip 10 is set on the chip holder 142 of the SPFS apparatus 100. In a case where a moisturizing agent is contained inside the channel 41 of the measuring chip 10, the inner side of the channel 41 is cleaned to remove the moisturizing agent.

Next, an angle of incidence of the excitation light $\alpha$ with respect to the metal film 30 (the film formation surface 22) of the measuring chip 10 is set to an enhancement angle (step S20). Specifically, the control unit 150 controls the conveyance stage 141 to move the measuring chip 10 to the measurement position from a position where the measuring chip 10 is disposed. Then, the control unit 150 controls the light source control unit 113 and the angle adjustment mechanism 112 to irradiate a predetermined position of the metal film 30 (the film formation surface 22) with the excitation light $\alpha$ from the light source unit 111, and to simultaneously change the angle of incidence of the excitation light $\alpha$ with respect to the metal film 30 (the film formation surface 22). At this time, the control unit 150 controls the position switching mechanism 122 to move the optical filter 125 out of the light path of the light receiving unit 121. At the same time, the control unit 150 controls the sensor control unit 123 to detect the plasmon scattering light γ with the light receiving sensor 127. The control unit 150 obtains data including a relationship between the angle of incidence of the excitation light α and the intensity of the plasmon scattering light γ. The control unit 150 then analyzes the data to determine the angle of incidence (enhancement angle) at which the intensity of the plasmon scattering light γ is maximized. Finally, the control unit 150 controls the angle mechanism 112 to set the angle of incidence of the excitation light α with respect to the metal film 30 (the film formation surface 22) to the enhancement angle.

Herein, the enhancement angle is determined by a material and shape of the prism 20, a thickness of the metal film 30, a refractive index of liquid inside the channel 41, and the like. However, the enhancement angle slightly varies depending on various factors such as a type and amount of the liquid inside the channel 41, and a shape error of the prism 20. For this reason, it is preferable to determine the enhancement angle for each measurement. The enhancement angle is determined by order of about 0.1 degrees.

Next, a sample and a second capture body are mixed outside the channel 41 and the second capture body is specifically bound to a part of an analyte in the sample (adjustment step (step S30)). A method for mixing the sample and the analyte is not particularly limited. For example, the control unit 150 may control the liquid-feeding-pump drive mechanism 133 to transfer the sample and the second capture body contained in separate containers or dispersion liquid thereof into one container of the liquid chip 131. Alternatively, the control unit 150 may control the liquid-feeding-pump drive mechanism 133 to suction both the sample and the second capture body into the single syringe 134.

Herein, the "second capture body" is a substance having a recognition site that specifically binds to a site where a first capture body is to bind in the analyte. As the sample and the second capture body are mixed, a part of the analyte in the sample binds to the second capture body. In other words, the "site where the first capture body is to bind" in a part of the analyte is blocked with the second capture body. Such a situation decreases an amount of the analyte capable of binding to the first capture body.

A type of the sample and that of the analyte provided to the channel 41 in the present embodiment is not particularly limited. Examples of the sample include body fluids such as blood, serum, plasma, urine, nasal discharge, saliva, and semen; and diluents of these body fluids. Examples of the analyte include nucleic acids (such as DNA, and RNA), proteins (such as polypeptides, and oligopeptides), amino acids, carbohydrates, lipids, and modified molecules of these materials.

The second capture body is not particularly limited as long as it is a substance having a recognition site that specifically binds to a site where the first capture body is to bind in the analyte. The second capture body may be, for example, an antibody similar to the first capture body (for example, a monoclonal antibody) or a fragment thereof. Alternatively, the second capture body may be an antibody different from the first capture body or a fragment thereof. Furthermore, the second capture body and a reagent containing the second capture body may be powdery or may be dispersed or dissolved in a solvent. In this step, the amount of the second capture body to be mixed in the sample is appropriately adjusted so as to set "the amount of the analyte capable of binding to the first capture body" within a desired range.

Next, a mixed solution of the sample and the second capture body is provided inside the channel 41 (binding step (step S40)). Specifically, the control unit 150 controls the conveyance stage 141 to move the measuring chip 10 from the measurement position to the liquid-feeding position. Then, the control unit 150 controls the liquid-feeding-pump drive mechanism 133 to provide into the channel 41 the mixed solution of the sample and the second capture body inside the liquid chip 131. Accordingly, the analyte in the sample specifically binds to the first capture body immobilized on the channel 41, and the analyte is immobilized on the metal film 30 (primary reaction).

After the primary reaction, an optical blank value is measured (step S50). Specifically, the control unit 150 controls the conveyance stage 141 to move the measuring chip 10 to the measurement position from a position where the measuring chip 10 is disposed. Then, the control unit 150 controls the light source control unit 113 to emit the excitation light α from the light source unit 111 toward the metal film 30 (the film formation surface 22). Simultaneously, the control unit 150 controls the sensor control unit 123 to detect light intensity of the light with the light receiving sensor 127, and records the light intensity as the blank value.

Furthermore, the analyte bound to the first capture body on the metal film 30 is labeled with a fluorescent substance (secondary reaction (step S60)). Specifically, the control unit 150 controls the conveyance stage 141 to move the measuring chip 10 from the measurement position to the liquid-feeding position. Then, the control unit 150 controls the liquid-feeding-pump drive mechanism 133 to provide a fluorescent labeling solution inside the liquid chip 131 into the channel 41. Accordingly, the analyte is labeled with the fluorescent substance. The fluorescent labeling solution is, for example, a buffer solution containing an antibody (secondary antibody) labeled with the fluorescent substance. The antibody labeled with the fluorescent substance specifically binds to a site of the analyte that is different from the site where the first capture body specifically binds. Then, the inner side of the channel 41 is cleaned with the buffer solution and the like to remove free fluorescent substances and the like.

Next, while the analyte labeled with the fluorescent substance is immobilized on the bottom face (the metal film 30) of the channel 41 through the first capture body, the metal film 30 (the film formation surface 22) is irradiated with the excitation light α through the prism 20. Then, a fluorescence value from the fluorescent substance that labels the analyte is measured (measurement step (step S70)). Specifically, the control unit 150 controls the conveyance stage 141 to move the measuring chip 10 from the liquid-feeding position to the measurement position. Then, the control unit 150 controls the light source control unit 113 to emit the excitation light α from the light source unit 111 toward the metal film 30 (the film formation surface 22). Simultaneously, the control unit 150 controls the sensor control unit 123 to detect light intensity of light having a wavelength equivalent to that of the fluorescence β with the light receiving sensor 127.

Finally, a signal value indicating the presence or amount of the analyte is calculated (step S80). The fluorescence value mainly includes the optical blank value as well as a fluorescent component (signal value) derived from the fluorescent substance that labels the analyte. Therefore, as the optical blank value obtained in step S50 is subtracted from the fluorescence value obtained in step S70, the control unit 150 can calculate a signal value correlated with the amount of the analyte. The signal value is converted into the amount or concentration of the analyte based on a calibration curve prepared in advance, while an additive amount and the like of the second capture body is also taken into consideration.

(Effect)

In a conventional SPFS apparatus, an increase in concentration of an analyte contained in a sample leads to an increase in light intensity of fluorescence to be detected. Therefore, an excessively high concentration of an analyte contained in a sample exceeds a dynamic range of a light receiving sensor, which may lead to inaccurate measurement. On the other hand, in the measurement method according to the first embodiment, the sample and the second capture body are mixed before the sample is provided to the channel 41, and the "site where the first capture body is to bind" in the analyte is blocked with the second capture body. Even though a high concentration of the analyte is contained in the target sample, the measurement method according to the first embodiment can reduce the amount of the analyte capable of binding to the first capture body so that the amount can be kept within the dynamic range of the measurement apparatus. Therefore, it is possible to measure the amount of the analyte with high accuracy without diluting the sample in multiple stages.

It should be noted that the measuring chip 10 used in the first embodiment may be combined with a reagent containing the second capture body, thereby forming a measuring kit. In the measuring kit, the reagent containing the second capture body may be in a powder state or liquid state.

In the aforementioned measurement method, the sample and the second capture body are mixed inside the liquid chip 131 or the syringe 134, but the sample and the second capture body may be mixed before being contained in the liquid chip 131.

Second Embodiment

A second embodiment is similar to the first embodiment except that a structure of a measuring chip 10' partially differs from the measuring chip 10 used for the measurement method in the first embodiment. Furthermore, an SPFS apparatus used herein is similar to the SPFS apparatus used in the first embodiment. Therefore, the measuring chip 10' used in the second embodiment will be mainly described, and the same reference numerals are given to structures similar to those in the first embodiment, and the description thereof will be omitted.

Figure 3:
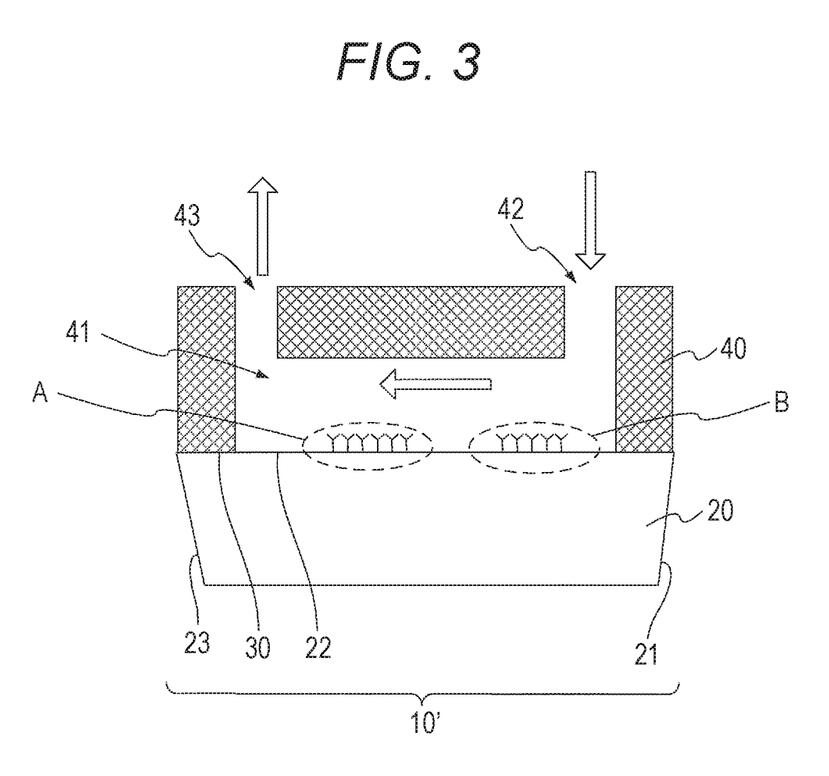
FIG. 3 is a schematic view illustrating an exemplary structure of a measuring chip used for measurement according to a second embodiment of the present invention.

FIG. 3 illustrates the measuring chip 10' used in the second embodiment. As similar to the measuring chip 10 in the first embodiment, the measuring chip 10' includes a prism 20 having an incidence surface 21, a film formation surface 22, and a light-emission surface 23; a metal film 30 formed on the film formation surface 22; and a channel cover 40 disposed on the film formation surface 22 or the metal film 30. The measuring chip 10' is usually exchanged per analysis. The measuring chip 10' is preferably a structural object having a length of several millimeters to several centimeters for each piece, but it may be a smaller structural object or a larger structural object not included in the category of "chip".

As illustrated in FIG. 3, a first capture body for capturing an analyte is immobilized in a detection area (represented by A in the drawing) of a surface of the metal film 30 not facing the prism 20 (a surface of the metal film 30). The "detection area" is provided to detect the analyte by the SPFS apparatus. A back side of the metal film 30 corresponding to the detection area A is irradiated with the excitation light α from a light source unit 111. The first capture body has a recognition site that specifically binds to the analyte. When the first capture body is immobilized on the detection area A of the metal film 30, the analyte in a sample specifically binds to the first capture body. Accordingly, the analyte is immobilized on the metal film 30 through the first capture body so as to be detected. The first capture body is not limited to a particular type as long as it can specifically bind to the analyte. The first capture body may be a biomolecule specific to the analyte (for example, a monoclonal antibody, polyclonal antibody, and nucleic-acid aptamer), or may be a fragment of the biomolecule.

In the present embodiment, a second capture body is also immobilized on an area out of the detection area (represented by B in FIG. 3) in a containing part 41 including the metal film 30 and the channel cover 40. In the present embodiment, the first capture body and the second capture body are exposed inside the containing part 41 so that when liquid is injected into the channel 41, the liquid comes into contact with the first capture body and the second capture body, which leads to various reactions and cleaning (removal of impurities).

Herein, the area B where the second capture body is immobilized is not particularly limited as long as it is outside the detection area A, that is, an area which is out of the area where the first capture body is immobilized and which is in contact with the sample. For example, the area B may be on the metal film 30, or may be a wall surface or a top face of a channel groove of the channel cover 40. In a case where the containing part 41 is a channel, and one end thereof is connected to a sample inlet 42, while the other end is connected to a sample outlet 43 (arrows in FIG. 3 indicate a direction in which the sample moves), the area B where the second capture body is immobilized may be either on a side close to the sample inlet 42 or a side close to the sample outlet 43. However, the area B is preferably on the side close to the sample inlet 42. When the second capture body is immobilized on the sample inlet 42, the analyte is likely to bind to the second capture body before the analyte binds to the first capture body. In other words, it is possible to reliably reduce an amount of the analyte capable of binding to the first capture body. An amount of the second capture body immobilized on the containing part 41 of the measuring chip 10' is appropriately selected in accordance with the amount of the analyte in the sample.

The second capture body is not particularly limited as long as it has a recognition site that specifically binds to the analyte. For example, the second capture body may be similar to the first capture body, or may be different from the first capture body. A site where the second capture body is to bind in the analyte may be the same as or different from a site where the first capture body is to bind in the analyte.

(Measurement Method)

Figure 4:
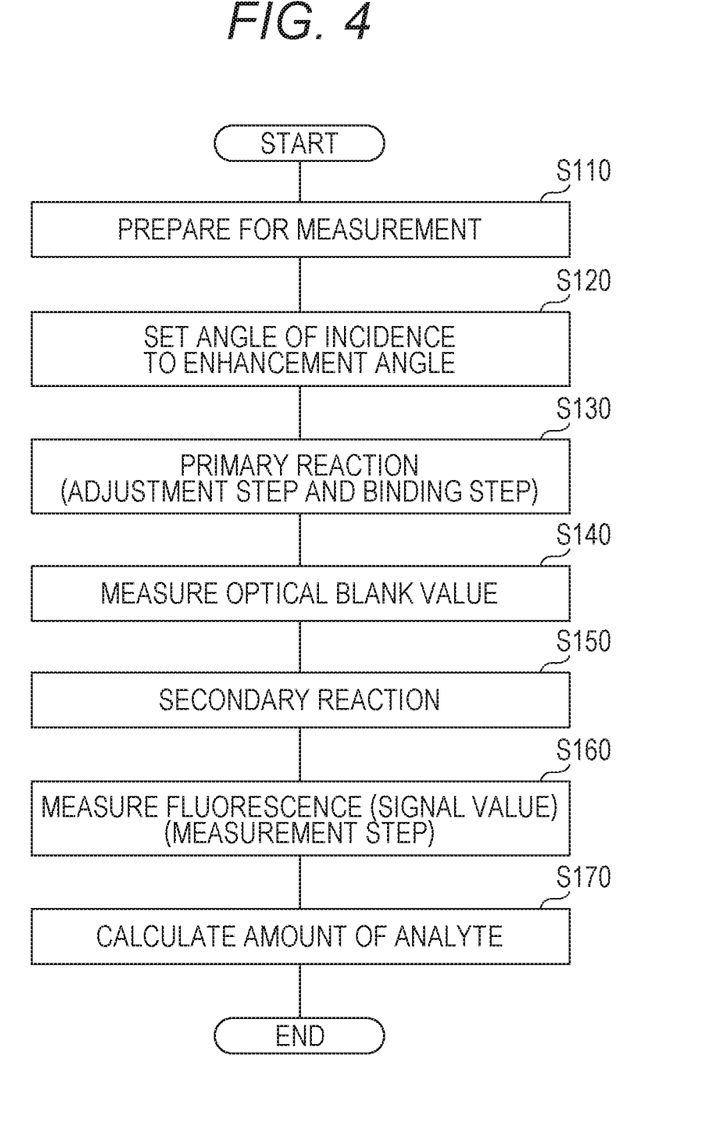
FIG. 4 is a flowchart illustrating an exemplary operation procedure of the SPFS apparatus when performing a measurement method according to the second embodiment of the present invention.

Hereinafter, a measurement method according to the second embodiment will be described. FIG. 4 is a flowchart illustrating an exemplary operation procedure of the SPFS apparatus 100 when performing the measurement method according to the present embodiment.

The first thing is to prepare for measurement (step S110). Specifically, a measuring chip 10' is set on the chip holder 142 of the SPFS apparatus 100. In a case where a moisturizing agent is contained inside the channel 41 of the measuring chip 10', the inner side of the channel 41 is cleaned to remove the moisturizing agent.

Next, an angle of incidence of the excitation light α with respect to the metal film 30 (the film formation surface 22) is set to an enhancement angle (step S120). This step is similar to the step in the first embodiment in which the enhancement angle is set (step S20).

Next, a sample is provided inside the channel 41 (adjustment step and binding step (step S130)). Specifically, the control unit 150 controls the conveyance stage 141 to move the measuring chip 10' from the measurement position to the liquid-feeding position. Then, the control unit 150 controls the liquid-feeding-pump drive mechanism 133 to provide the sample in the liquid chip 131 into the channel 41. Accordingly, a part of an analyte in the sample specifically binds to a second capture body immobilized on the area B out of the detection area in the channel 41 (the containing part 41), which decreases an amount of the analyte capable of binding to a first capture body. Then, the remaining analyte in the sample specifically binds to the first capture body immobilized on the detection area A in the channel 41. In other words, the analyte is captured on the detection area A of the metal film 30 (primary reaction). A type of the sample and that of the analyte provided to the channel 41 in this step are not particularly limited, and may be similar to the sample and the analyte provided to the channel 41 by the measurement method according to the first embodiment.

After the primary reaction, an optical blank value is measured (step S140). This step is similar to the step in the first embodiment in which the optical blank value is measured (step S50). Next, the analyte bound to the first capture body on the metal film 30 is labeled with a fluorescent substance (secondary reaction (step S150)). This step is similar to the step in the first embodiment (secondary reaction (step S60)).

Next, while the analyte labeled with the fluorescent substance is immobilized on the bottom face (the metal film 30) of the channel 41 through the first capture body, the detection area of the metal film 30 (the film formation surface 22) is irradiated with the excitation light α through the prism 20. Then, a fluorescence value from the fluorescent substance labeling the analyte in the detection area is measured (step S160). This step is similar to the measurement step in the first embodiment (step S70).

Finally, a signal value indicating the presence or amount of the analyte is calculated (step S170). The fluorescence value mainly includes the optical blank value as well as a fluorescent component (signal value) derived from the fluorescent substance that labels the analyte. Therefore, as the optical blank value obtained in step S140 is subtracted from the fluorescence value obtained in step S160, the control unit 150 can calculate a signal value correlated with the amount of the analyte. The signal value is converted into the amount or concentration of the analyte based on a calibration curve prepared in advance, while an amount of the second capture body immobilized on the measuring chip 10' is taken into consideration.

(Effect)

As described above, in the measurement method according to the second embodiment, the second capture body immobilized on the containing part captures the analyte contained in the sample so as to reduce the amount of the analyte capable of binding to the first capture body. Therefore, in the measurement method according to the second embodiment, even though a high concentration of the analyte is contained in the target sample, the amount of the analyte capable of binding to the first capture body is set within a dynamic range of the measurement apparatus. Accordingly, the amount of the analyte can be measured with high accuracy.

In the aforementioned description, the second capture body is immobilized on the area B out of the detection area in the containing part 41, but a position to immobilize the second capture body is not limited to the inner side of the measuring chip 10'. For example, the second capture body may be immobilized on a member other than the containing part 41. The member where the second capture body is immobilized is not particularly limited as long as it can be brought into contact with the sample before the binding step (step S130). For example, the member may be the liquid chip 131 or the syringe 134. In this case, it is possible to reduce the amount of the analyte to be provided to the containing part 41 of the measuring chip 10' without immobilizing the second capture body on the measuring chip 10'. Therefore, it is possible to keep the amount of the analyte capable of binding to the first capture body within the dynamic range of the measurement apparatus, which makes it possible to measure the amount of the analyte with high accuracy without diluting the sample in multiple steps.

Other Embodiments

Figure 5:
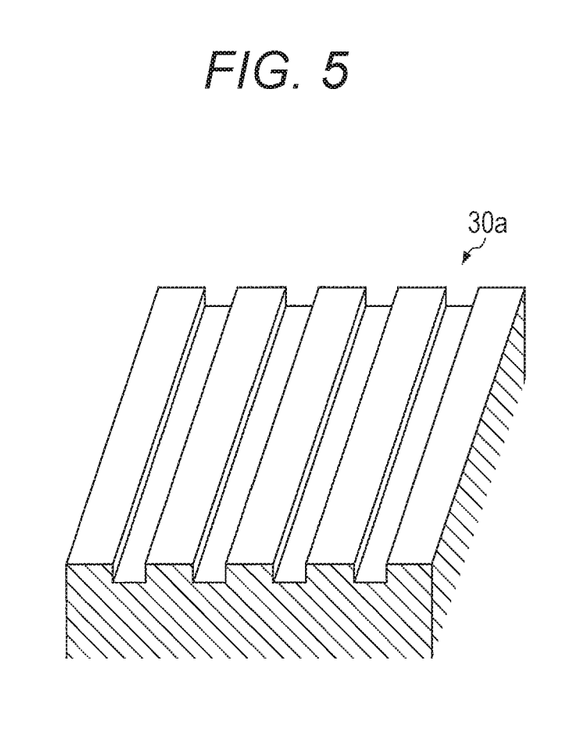
FIG. 5 is a perspective view of a metal film including a diffraction grating.

Described in the first and second embodiments are the measurement methods and the measurement apparatuses utilizing the prism coupling (PC)-SPFS in which the prism 20 formed with the metal film 30 is used to bind (couple) photons and surface plasmons. However, a measurement method and a measuring chip according to the present invention are not limited to these embodiments. FIG. 5 is a perspective view of a metal film 30a including a diffraction grating. As illustrated in FIG. 5, a measurement method and a measurement apparatus according to the present invention may use a measuring chip having the metal film 30a including the diffraction grating. Even in this case, it is possible to bind photons and surface plasmons and to emit plasmon scattering light γ from the metal film 30a. In this case, the prism 20 is not required. Furthermore, an excitation light irradiation unit 110 is disposed on a side close to the metal film 30a of the measuring chip, being configured to irradiate the diffraction grating with the excitation light α in a step of detecting fluorescence β and in a step of detecting the plasmon scattering light γ.

Described in the first and second embodiments are the measurement methods using the SPFS apparatus, the measuring chips, and the measuring kit, but a measurement method, a measuring chip, and a measuring kit according to the present invention are not limited to these embodiments. The measurement method may also be applied to the ELISA, the RIfS, the SPR, the QCM, and the like. Furthermore, the measuring chip and the measuring kit may be configured to have a structure suitable for to these measurement methods.

EXAMPLES

Hereinafter, the present invention will be described in detail with reference to Examples, but the present invention is not limited by these Examples.

1. Measurement of Concentration of Cystatin C According to First Embodiment (1) Preparation of Measuring Chip A measuring chip including a metal film was prepared on one surface of a prism. An anti-cystatin C antibody was immobilized on a detection area of the metal film of the prism. A channel cover was placed on the metal film to form the measuring chip. The measuring chip was set on a chip holder of an SPFS apparatus.

(2) Adjustment Step

Samples 1A to 7A containing cystatin C, an analyte, at a predetermined concentration were prepared in an amount of 5 μL each (Table 1 illustrates a concentration of cystatin C contained in each sample). Each sample was mixed with 445

μL of a reaction solution (PBS containing 0.05% Tween, 3% BSA, and 10 μg/mL of anti-cystatin C antibody, pH 7.4). The anti-cystatin C antibody contained in the reaction solution was the same antibody as the anti-cystatin C antibody immobilized on the measuring chip.

(3) Binding Step and Measurement Step

A mixed solution of each sample and the reaction solution in an amount of 150 μL was fed back and forth into the channel of the measuring chip so as to allow cystatin C in the mixed solution to specifically react with the anti-cystatin C antibody immobilized on the detection area in the channel (primary reaction).

Subsequently, the sample in the channel was removed, and the inner side of the channel was cleaned with a cleaning solution (PBS containing 0.05% Tween, pH 7.4). Then, a measurement solution (PBS containing 0.05% Tween and 5% BSA, pH 7.4) was provided inside the channel, and the metal film was irradiated from the prism with excitation light having a wavelength of 635 nm at an enhancement angle. Light emitted from a reaction field was detected to obtain an optical blank value.

Then, a solution (40 μL) containing an anti-cystatin C antibody labeled with Alexa-Fluor (registered trademark) as a fluorescent substance was fed back and forth into the channel so as to allow cystatin C immobilized on the detection area to specifically react with the anti-cystatin C antibody labeled with the fluorescent substance (secondary reaction).

After the secondary reaction, the solution in the channel was removed, and the inner side of the channel was cleaned with a cleaning solution as similar to the above. Then, as similar to the measurement of the optical blank value, a measurement solution was provided inside the channel, and the metal film was irradiated with excitation light to detect fluorescence emitted from the reaction field. The optical blank value was subtracted from a detected value of the fluorescence to obtain a signal value indicating an amount of cystatin C.

2. Measurement of Concentration of Cystatin C According to a Typical Method (1) Preparation of Measuring Chip As similar to Example 1, a measuring chip was prepared and set on the chip holder of the SPFS apparatus.

(2) Binding Step and Measurement Step

Samples 1B to 8B containing cystatin C, an analyte, at a predetermined concentration were prepared in an amount of 5 μL each (Table 1 illustrates a concentration of cystatin C contained in each sample). Each sample was mixed with 445 μL of a diluted solution (PBS containing 0.05% Tween and 3% BSA, pH 7.4). A reaction was performed in steps similar to Example 1 except that this mixed solution was fed back and forth into the channel of the measuring chip so as to allow cystatin C in the mixed solution to specifically react with an anti-cystatin C antibody immobilized on the detection area in the channel (primary reaction), thereby obtaining a signal value indicating an amount of cystatin C.

TABLE 1

| Sample No. | | Concentration of Cystatin C (ng/mL) |
|---|---|---|
| Sample 1A | Sample 1B | 30000 |
| Sample 2A | Sample 2B | 20000 |
| Sample 3A | Sample 3B | 10000 |
| Sample 4A | Sample 4B | 5500 |
| Sample 5A | Sample 5B | 1100 |
| Sample 6A | Sample 6B | 110 |

TABLE 1-continued

| Sample No. | | Concentration of Cystatin C (ng/mL) |
|---|---|---|
| Sample 7A | Sample 7B | 11 |
| — | Sample 8B | 1.1 |

3. Results

Figure 6:
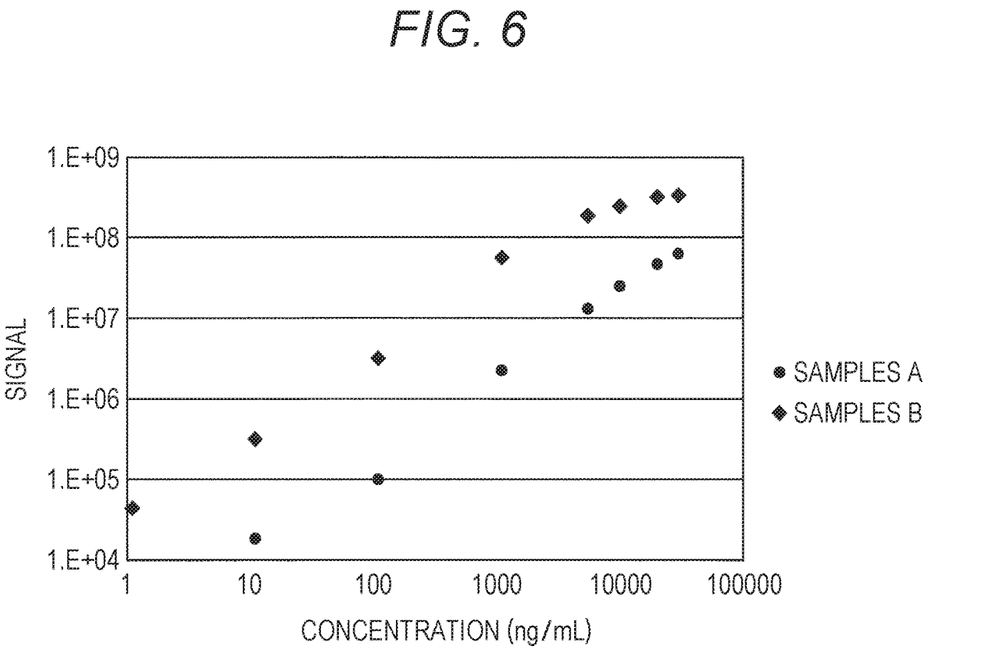
FIG. 6 is a graph illustrating a relationship between a signal value indicating an amount of cystatin C and a concentration of cystatin C contained in a sample.

FIG. 6 is a graph illustrating a relationship between the concentration of cystatin C contained in each sample and the signal value indicating the amount of cystatin C. The samples A (represented by circles) in FIG. 6 are measurement results when the reaction solution containing the anti-cystatin C antibody is added to the samples. The samples B (represented by rhombuses) in FIG. 6 are measurement results when the diluted solution not containing the anti-cystatin C antibody is added to the samples. In FIG. 6, the concentration (ng/mL) of cystatin C contained in each sample is taken along the abscissa, and the signal value indicating the amount of cystatin C is taken along the ordinate. As illustrated in FIG. 6, in both the samples A and the samples B, as the concentration of cystatin C increases, the signal value increases. However, as seen in the signal value of the samples B, when the anti-cystatin C antibody is not added to the samples in advance, saturation of the signal value can be observed in a high concentration area. On the other hand, as seen in the signal value of the samples A in FIG. 6, when the anti-cystatin C antibody is added to the samples in advance, saturation of the signal value is suppressed even in the high concentration area, and the signal value corresponding to the concentration is obtained. In other words, it seems that the amount of the analyte can be measured with high accuracy even in the high concentration region.

4. Measurement of Concentration of Cystatin C According to Second Embodiment (1) Preparation of Measuring Chip A measuring chip including a metal film was prepared on one surface of a prism. An anti-cystatin C antibody was immobilized on a detection area of the metal film of the prism. Furthermore, the anti-cystatin C antibody was immobilized on an area right before the detection area, that is, an area (metal film) on the upstream of the detection area when providing a sample to a channel. A channel cover was placed on the metal film to form the measuring chip. The measuring chip was set on a chip holder of an SPFS apparatus.

(2) Adjustment Step, Binding Step, and Measurement Step

Samples 1C to 5C containing cystatin C, an analyte, at a predetermined concentration were prepared in an amount of 5 μL each (Table 2 illustrates a concentration of cystatin C contained in each sample). Each sample was mixed with 445 μL of a diluted solution (PBS containing 0.05% Tween and 3% BSA, pH 7.4). Subsequently, a reaction was performed in steps similar to Example 1 except that this mixed solution was fed back and forth into the channel of the measuring chip so as to allow cystatin C in the mixed solution to specifically react with the anti-cystatin C antibody immobilized on the detection area in the channel (primary reaction), thereby obtaining a signal indicating the amount of the cystatin C.

5. Measurement of Concentration of Cystatin C According to a Typical Method (1) Preparation of Measuring Chip As similar to Example 1, a measuring chip was prepared and set on the chip holder of the SPFS apparatus.

(2) Binding Step and Measurement Step

Samples 1D to 8D containing cystatin C, an analyte, at a predetermined concentration were prepared in an amount of 5 μL each (Table 2 illustrates a concentration of cystatin C contained in each sample). Each sample was mixed with 445 μL of a diluted solution (PBS containing 0.05% Tween and 3% BSA, pH 7.4). Subsequently, a reaction was performed in steps similar to Example 1 except that this mixed solution was fed back and forth into the channel of the measuring chip so as to allow cystatin C in the mixed solution to specifically react with the anti-cystatin C antibody immobilized on the detection area in the channel (primary reaction), thereby obtaining a signal indicating the amount of the cystatin C.

TABLE 2

| Sample No. | | Concentration of Cystatin C (ng/mL) |
|---|---|---|
| Sample 1C | Sample 1D | 30000 |
| — | Sample 2D | 20000 |
| Sample 2C | Sample 3D | 10000 |
| — | Sample 4D | 5500 |
| Sample 3C | Sample 5D | 1100 |
| Sample 4C | Sample 6D | 110 |
| Sample 5C | Sample 7D | 11 |
| — | Sample 8D | 1.1 |

6. Results

Figure 7:
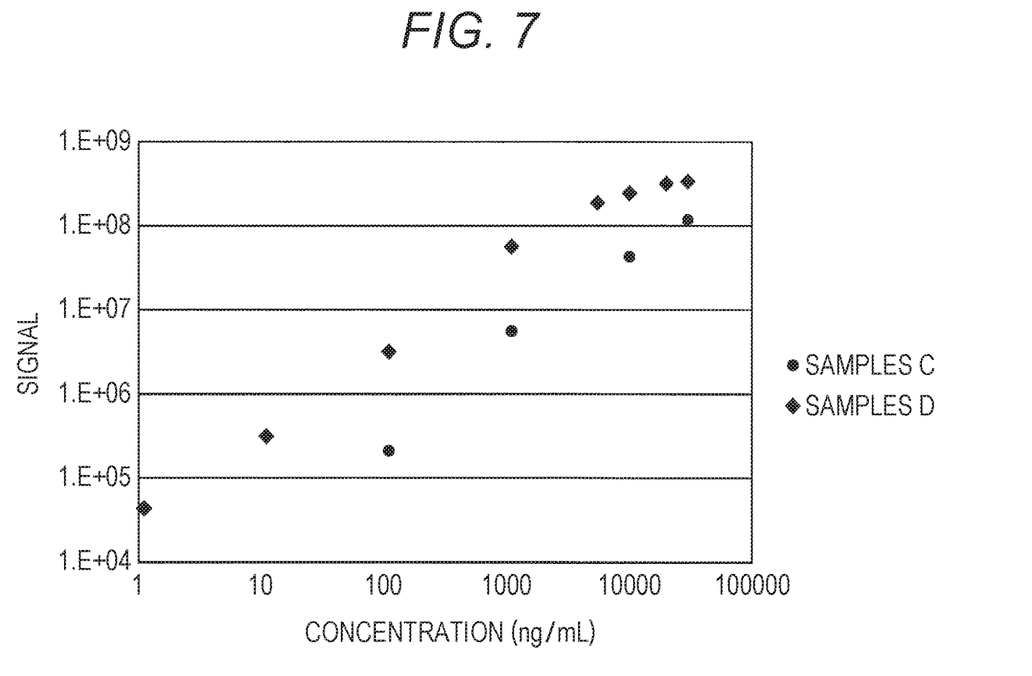
FIG. 7 is a graph illustrating a relationship between a signal value indicating an amount of cystatin C and a concentration of cystatin C contained in a sample.

FIG. 7 is a graph illustrating a relationship between the concentration of cystatin C contained in each sample and the signal value indicating the amount of cystatin C. The samples C (represented by circles) in FIG. 7 are measurement results when the anti-cystatin C antibody is also immobilized on the channel other than the detection area of the measuring chip. The samples D (represented by rhombuses) in FIG. 7 are measurement results when the anti-cystatin C antibody is immobilized only in the detection area.

In FIG. 7, the concentration (ng/mL) of cystatin C contained in each sample is taken along the abscissa, and the signal value indicating the amount of cystatin C is taken along the ordinate. As illustrated in FIG. 7, in both the samples C and the samples D, as the concentration of cystatin C increases, the signal value increases. However, as seen in the signal value of the samples D, when the anti-cystatin C antibody is not immobilized on the channel other than the detection area, saturation of the signal value can be observed in a high concentration area. On the other hand, as seen in the signal value of the samples C in FIG. 7, when the anti-cystatin C antibody is immobilized on the channel other than the detection area, saturation of the signal value is suppressed even in the high concentration area, and the signal value corresponding to the concentration is obtained. In other words, it seems that the amount of the analyte can be measured with high accuracy even in the high concentration region.

As seen from the above results, in a case where a sample contains a high concentration of an analyte, employing the measurement method according to the first embodiment or the second embodiment of the present invention makes it possible to measure an amount of the analyte with accuracy without multistage dilution.

This application claims priority based on JP 2015-126748 A filed on Jun. 24, 2015. The contents Industrial Applicability A measurement method for an analyte, a measuring chip, and a measuring kit according to the present invention make it possible to detect an analyte with high reliability without multistage dilution so that the measurement method, measuring chip, and the measuring kit are useful for examining diseases and the like.

REFERENCE SIGNS LIST 10, 10' Measuring chip
20 Prism
21 Incidence surface
22 Film formation surface
23 Light-emission surface
30 Metal film
40 Channel cover
41 Containing part (channel)
100 SPFS apparatus
110 Excitation light irradiation unit
111 Light source unit
112 Angle adjustment mechanism
113 Light source control unit
120 Fluorescence detection unit
121 Light receiving unit
122 Position switching mechanism
123 Sensor control unit
124 First lens
125 Optical filter
126 Second lens
127 Light receiving sensor
130 Liquid feeding unit
131 Liquid chip
132 Syringe pump
133 Liquid-feeding-pump drive mechanism
134 Syringe
135 Plunger
140 Conveyance unit
141 Conveyance stage
142 Chip holder
150 Control unit
α Excitation light
β Fluorescence
γ Plasmon scattering light

The invention claimed is:

1. A measurement method for measuring an amount of an analyte in a sample, the method comprising:
    binding the analyte contained in the sample to a first capture body immobilized inside a containing part for containing liquid and having a recognition site that specifically binds to the analyte by providing the sample to the containing part of a measuring chip including the containing part and the first capture body; and
    measuring an amount of the analyte bound to the first capture body,
    the measurement method further comprising:
    reducing the amount of the analyte capable of binding to the first capture body by binding a second capture body having a recognition site that specifically binds to the analyte to a part of the analyte in the sample before the binding,
    wherein the second capture body has a recognition site that specifically binds to a site where the first capture body is to bind in the analyte, and
    the reducing includes mixing the second capture body with the sample before being provided to the containing part.

2. The measurement method according to claim 1, wherein the reducing includes bringing the sample into contact with a member where the second capture body is immobilized.

3. The measurement method according to claim 1, further comprising labeling the analyte bound to the first capture body with a fluorescent substance before the measuring.

4. The measurement method according to claim 3, wherein the measuring chip includes a prism including a dielectric material, the containing part disposed on one surface of the prism, a metal film disposed on a bottom face of the containing part, and the first capture body immobilized on the metal film, and
the measuring includes irradiating the metal film with light so as to generate surface plasmon resonance while the analyte is immobilized on the metal film through the first capture body, so as to detect fluorescence emitted from the fluorescent substance that labels the analyte.

5. The measurement method according to claim 3, wherein the measuring chip includes the containing part, a metal film disposed on a bottom face of the containing part and including a diffraction grating, and the first capture body immobilized on the metal film, and
the measuring includes irradiating the metal film with light so as to generate surface plasmon resonance while the analyte is immobilized on the metal film through the first capture body, so as to detect fluorescence emitted from the fluorescent substance that labels the analyte.

6. A measuring chip for measuring an amount of an analyte in a sample, the measuring chip comprising:
a containing part for containing liquid;
a first capture body immobilized on a detection area for detecting an analyte inside the containing part and having a recognition site that specifically binds to the analyte; and
a second capture body immobilized on an area out of the detection area inside the containing part and having a recognition site that specifically binds to the analyte,
wherein the measuring chip is configured such that:
the amount of the analyte capable of binding to the first capture body is reduced by binding a second capture body having a recognition site that specifically binds to the analyte to a part of the analyte in the sample before the binding,
wherein the reducing includes mixing the second capture body with the sample before being provided to the containing part.

7. The measuring chip according to claim 6, comprising:
a prism including a dielectric material;
the containing part disposed on one surface of the prism;
a metal film disposed on a bottom face of the containing part;
the first capture body immobilized on the metal film; and
the second capture body immobilized on the area out of the detection area in the containing part.

8. The measuring chip according to claim 6, comprising:
the containing part;
a metal film disposed on a bottom face of the containing part and including a diffraction grating;
the first capture body immobilized on the metal film; and
the second capture body immobilized on the area out of the detection area in the containing part.

9. A measuring kit comprising:
a measuring chip which includes a containing part for containing liquid, and a first capture body which is immobilized on a detection area for detecting an analyte inside the containing part and has a recognition site that specifically binds to the analyte; and
a reagent including a second capture body having a recognition site that specifically binds to a site where the first capture body is to bind in the analyte,
wherein the measuring chip is configured such that:
an amount of the analyte capable of binding to the first capture body is reduced by binding the second capture body having the recognition site that specifically binds to the analyte to a part of the analyte in a sample in parallel with the binding or before the binding, and
the reducing includes mixing the second capture body with the sample before being provided to the containing part.

10. The measurement method according to claim 1, further comprising labeling the analyte bound to the first capture body with a fluorescent substance before the measuring.

11. The measurement method according to claim 2, further comprising labeling the analyte bound to the first capture body with a fluorescent substance before the measuring.

* * * * *